United States Patent
Amancha et al.

(10) Patent No.: US 9,642,848 B2
(45) Date of Patent: May 9, 2017

(54) SUBLINGUAL NALOXONE SPRAY

(71) Applicant: Insys Pharma, Inc., Chandler, AZ (US)

(72) Inventors: Kiran Amancha, Chandler, AZ (US); Shivani Chilampalli, Phoenix, AZ (US); Thrimoorthy Potta, Chandler, AZ (US); Ningxin Yan, Chandler, AZ (US); Venkat R. Goskonda, Phoenix, AZ (US)

(73) Assignee: Insys Development Company, Inc., Chandler, AZ (US)

( * ) Notice: Subject to any disclaimer, the term of this patent is extended or adjusted under 35 U.S.C. 154(b) by 0 days.

(21) Appl. No.: 14/730,585

(22) Filed: Jun. 4, 2015

(65) Prior Publication Data

US 2016/0008349 A1 Jan. 14, 2016

Related U.S. Application Data

(60) Provisional application No. 62/022,041, filed on Jul. 8, 2014.

(51) Int. Cl.
*A61K 31/485* (2006.01)
*A61K 47/10* (2006.01)
*A61K 9/00* (2006.01)

(52) U.S. Cl.
CPC ............ *A61K 31/485* (2013.01); *A61K 9/006* (2013.01); *A61K 47/10* (2013.01)

(58) Field of Classification Search
CPC ....... A61K 31/485; A61K 9/006; A61K 47/10
See application file for complete search history.

(56) References Cited

U.S. PATENT DOCUMENTS

| | | |
|---|---|---|
| 6,365,596 B1 | 4/2002 | Valenti |
| 6,413,496 B1 | 7/2002 | Goodman et al. |
| 7,501,113 B2 | 3/2009 | Blondino et al. |
| 8,017,150 B2 | 9/2011 | Yang et al. |
| 8,211,946 B2 | 7/2012 | Whittle |
| 8,454,996 B2 | 6/2013 | Pettersson et al. |
| 8,470,361 B2 | 6/2013 | Pettersson |
| 8,475,832 B2 | 7/2013 | Myers et al. |
| 8,603,514 B2 | 12/2013 | Yang et al. |
| 8,658,198 B2 | 2/2014 | Pettersson |
| 8,980,305 B2 | 3/2015 | Petterssson |
| 2003/0190290 A1 | 10/2003 | Ross |
| 2004/0039366 A1 | 2/2004 | MacLeod |
| 2007/0148097 A1 | 6/2007 | Finn et al. |
| 2007/0261695 A1* | 11/2007 | Kottayil ............. A61K 9/006 128/200.21 |
| 2009/0270438 A1 | 10/2009 | Booles et al. |
| 2010/0015183 A1 | 1/2010 | Finn et al. |
| 2010/0087470 A1 | 4/2010 | Oksche et al. |
| 2010/0120812 A1 | 5/2010 | Chapleo et al. |
| 2011/0189259 A1 | 8/2011 | Vasisht et al. |
| 2012/0070495 A1* | 3/2012 | Shah ................ A61K 9/2054 424/465 |
| 2012/0217184 A1* | 8/2012 | Edwards ............ A61M 5/2033 206/571 |
| 2013/0071477 A1* | 3/2013 | Fischer ................ A61K 9/14 424/465 |
| 2013/0109747 A1 | 5/2013 | Whittle |
| 2014/0005218 A1 | 1/2014 | Myers et al. |

FOREIGN PATENT DOCUMENTS

| | | |
|---|---|---|
| CN | 101057830 | 10/2007 |
| WO | WO 00/35456 | 6/2000 |
| WO | WO 2009/120889 | 10/2009 |
| WO | WO 2014/071499 | 5/2014 |

OTHER PUBLICATIONS

English Translation of CN 101057830, Machine Translated Apr. 19, 2016.*
ISR and Written Opinion in corresponding application No. PCT/US2015/03418 issued Aug. 26, 2015.
Yanagida, "Congenital insensitivity and naloxone", Lancet, Sep. 1978, vol. 312(8088), pp. 520-521.

* cited by examiner

*Primary Examiner* — James D Anderson
(74) *Attorney, Agent, or Firm* — Wood, Phillips, Katz, Clark & Mortimer

(57) ABSTRACT

The invention provides storage stable sublingual formulations containing naloxone, a pharmaceutically acceptable salt or a derivative thereof. The invention further provides methods for treating opioid dependence, opioid overdose, and congenital insensitivity to pain with anhidrosis by administering the sublingual formulations of the present invention to a patient in need thereof.

6 Claims, No Drawings

SUBLINGUAL NALOXONE SPRAY

FIELD OF THE INVENTION

The invention is directed to sublingual spray formulations containing naloxone, a pharmaceutically acceptable salt thereof, or a derivative thereof. The invention is further directed to methods of treating opioid dependence, opioid overdose, and congenital insensitivity to pain with anhidrosis by administering sublingual spray formulations containing naloxone, pharmaceutically acceptable salts thereof, or derivatives thereof to a patient in need thereof.

BACKGROUND OF THE INVENTION

Naloxone has the following structure and is synthesized from thebaine:

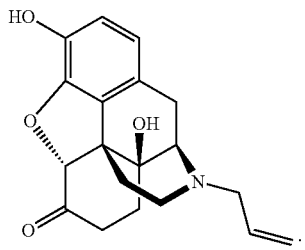

Naloxone is most commonly used to treat patients suffering from opioid dependence or overdose because it is a competitive μ-opioid antagonist that blocks the effects of opioids. Naloxone is currently available in Suboxone® (Suboxone is a registered trademark of Reckitt Benckiser Healthcare (UK) Limited) as tablet or sublingual film strip formulations. Suboxone® contains buprenorphine and naloxone in a 4:1 ratio.

One issue with other opioid dependence treatments is that they can become addictive. Naloxone, however, does not appear to be addictive and patients do not build up a tolerance.

Naloxone has also been used as a treatment for cognitive insensitivity to pain with anhidrosis. Insensitivity to pain with cognitive anhidrosis is a disorder in which the patient cannot feel pain.

Naloxone may be administered orally, intravenously, by injection or via the nasal mucosa. Naloxone has a low mean serum half-life when administered parentally. The quick metabolism may require repeat dosing or cause patient discomfort between doses. Enteral administration has low bioavailability due to hepatic first pass metabolism.

Accordingly, while there are some naloxone formulations currently available, there is a need for safe and effective sublingual spray formulations that are storage stable and contain naloxone, pharmaceutically acceptable salts or a derivative thereof.

SUMMARY OF THE INVENTION

In one aspect, the invention is directed to storage stable sublingual spray formulations comprising an effective amount of naloxone, a pharmaceutically acceptable salt or a derivative thereof, water, cosolvent and an antioxidant.

In another aspect, the invention is directed to storage stable sublingual spray formulations comprising an effective amount of naloxone, a pharmaceutically acceptable salt or a derivative thereof, water and an antioxidant that do not contain alcohol.

In yet another aspect, the invention is directed to methods for treating opioid dependence comprising administering the sublingual spray formulations of the present invention to a patient in need of opioid dependence treatment.

In a further aspect, the invention is directed to methods for treating opioid overdose comprising administering the sublingual spray formulations of the present invention to a patient in need of opioid overdose treatment.

In an additional aspect, the invention is directed to methods for treating congenital insensitivity to pain with anhidrosis comprising administering the sublingual spray formulations of the present invention to a patient in need of treatment for congenital insensitivity to pain with anhidrosis.

DETAILED DESCRIPTION OF THE INVENTION

Applicants have created new sublingual naloxone formulations which have high bioavailability, are storage stable, and have excellent droplet distribution when administered. Applicant created stable formulations with and without alcohol (see Examples 1, 4 and 5). The formulations that do not contain alcohol are especially suitable for administration to children. Further, the alcohol-free formulations may be suitable for patients in recovery from alcohol addiction.

Formulations with Alcohol

In one embodiment, the invention is directed to sublingual spray formulations comprising an effective amount of naloxone, a pharmaceutically acceptable salt or a derivative thereof, water as a solvent, a cosolvent and an antioxidant. In a preferred embodiment, naloxone is in salt form.

The cosolvent may be a mixture of an alcohol and a glycol, or a mixture thereof. The formulations preferably contain from about 5 to about 90% w/w cosolvent. More preferably the formulations contain from about 20% to about 70% or from about 40% to about 65% w/w cosolvent. In a most preferred embodiment, the formulations contain about 60% w/w cosolvent.

Suitable antioxidants include butylated hydroxyanisole (BHA), butylated hydroxytoluene (BHT), methionine, sodium ascorbate, sodium thiosulfate, thioglycerol, and a combination thereof. Presently preferred antioxidants include BHA, BHT, sodium thiosulfate and sodium ascorbate.

In a preferred embodiment, the amount of antioxidant included in the formulation is from about 0.001% to about 0.05% w/w.

In another preferred embodiment, the amount of antioxidant is about 0.01% w/w of BHA.

In an alternative embodiment, the antioxidant is a mixture of about 0.01% w/w of BHA and about 0.005% w/w of BHT.

In yet another embodiment, the antioxidant is about 0.01% w/w of sodium thiosulfate.

In another preferred embodiment, the antioxidant is about 0.02% w/w of sodium ascorbate.

Water is used in the present formulations as the solvent. Preferably, from about 10% to about 95% w/w water is in the formulations. More preferably, from about 20% to about 80% w/w water is in the formulations. Even more preferably, from about 25% to about 45% w/w water is in the formulations. In most preferred embodiments, the formulations contain about from about 30% to about 40% w/w water, or about 29.8%, 33.2%, 34.5% or 37.5% w/w water.

In a preferred embodiment, the formulations of the present invention have a pH of from about 2 to about 7. In a more preferred embodiment, the formulations of the present invention have a pH of from about 4 to about 6.

In another preferred embodiment, the formulations contain ethanol as the alcohol.

In yet another preferred embodiment, the formulations contain propylene glycol as the glycol.

In another embodiment, the formulations of the present invention contain a chelating agent. In a preferred embodiment, the chelating agent is edetate disodium dihydrate.

In an embodiment, the formulations contain from about 0.001% to about 0.5% w/w of the chelating agent. In a preferred embodiment, the formulations contain from about 0.001% w/w to about 0.10% of the chelating agent. In a more preferred embodiment, the formulations contain from about 0.002% to about 0.1% w/w of the chelating agent. In a more preferred embodiment, the formulations contain from about 0.002 to about 0.008% w/w of the chelating agent.

In a preferred embodiment, the present invention is directed to sublingual spray formulation comprising naloxone, a pharmaceutically acceptable salt or a derivative thereof, in an amount from about 0.01% to about 15% w/w, water in an amount from about 10% to about 95% w/w, a cosolvent in an amount from about 5% to about 90% w/w, an antioxidant in an amount from about 0.0001% to about 0.1% w/w, and a chelating agent in an amount from about 0.001% to 0.5%, wherein the % w/w is of the total formulation. In a preferred embodiment, the formulation also contains menthol in an amount from about 0.001% to about 0.1% w/w. In another preferred embodiment, the formulation contains edetate disodium dihydrate as the chelating agent.

In yet another embodiment, the present invention is directed to naloxone, a pharmaceutically acceptable salt or a derivative thereof, in an amount from about 1% to about 15% w/w, water in an amount from about 20% to about 80% w/w, a cosolvent in an amount from about 5% to about 90% w/w, an antioxidant in an amount from about 0.001% to about 0.1% w/w, and a chelating agent in an amount from about 0.001% to 0.5%, wherein the % w/w is of the total formulation. In a preferred embodiment of the formulation, naloxone is a salt. In yet another preferred embodiment, the formulation also contains menthol in an amount from about 0.01% to about 0.1% w/w. In another preferred embodiment, the formulation contains edetate disodium dihydrate as the chelating agent.

In a further embodiment, the present invention is directed to naloxone, a pharmaceutically acceptable salt or a derivative thereof in an amount from about 1% to about 12% w/w, water in an amount from about 25% to about 45% w/w, a cosolvent in an amount from about 40% to about 75% w/w, an antioxidant in an amount from about 0.005% to about 0.08% w/w, and a chelating agent in an amount from about 0.001% to 0.5% w/w, wherein the % w/w is of the total formulation. In a preferred embodiment of this formulation, naloxone is a salt. In another preferred embodiment, the formulation also contains menthol in an amount from about 0.02% to about 0.08% w/w. In yet another preferred embodiment, the formulation contains edetate disodium dihydrate as the chelating agent.

In another embodiment, the present invention is directed to formulations wherein the cosolvent is a mixture of ethanol and propylene glycol.

In a preferred embodiment, the formulations of the present invention are directed to sublingual spray formulations wherein the amount of naloxone salt is from about 2% to about 3% w/w, the amount of water is from about 35% to about 40% w/w, the amount of cosolvent is from about 50% to about 70% w/w, and the amount of antioxidant is about 0.01% w/w, wherein the % w/w is of the total formulation. Preferably, the cosolvents are ethanol and propylene glycol and the ethanol is from about 50% to about 60% w/w and the propylene glycol is from about 3% to about 7% w/w. Preferably, the formulation contains about 2.4% w/w naloxone, about 37.5% w/w water, about 55% w/w ethanol, and about 5% propylene glycol. In an embodiment, the formulation also contains about 0.005% or 0.02% w/w disodium edetate dihydrate.

In an embodiment, the formulations of the present invention are directed to sublingual spray formulations wherein the amount of naloxone salt is from about 5% to about 8% w/w, the amount of water is from about 30% to about 35% w/w, the ethanol is from about 50% to about 60% w/w, the propylene glycol is from about 3% to about 7% w/w, and the antioxidant is from about 0.01% to about 0.03% w/w, wherein the % w/w is of the total formulation. Preferably, this formulation contains about 6.7% w/w naloxone salt, about 33.2% w/w water, about 55% w/w ethanol, and about 5% propylene glycol. In an embodiment, the formulation also contains about 0.005% w/w or 0.02% disodium edetate dihydrate.

In a preferred embodiment, the formulations of the present invention are directed to sublingual spray formulations wherein the amount of naloxone is from about 3% to about 5% w/w, the amount of water is from about 35% to about 40% w/w, the amount of cosolvent is from about 50% to about 70% w/w, and the amount of antioxidant, sodium ascorbate, is about 0.02% w/w, wherein the % w/w is of the total formulation. Preferably, the cosolvents in this formulation are ethanol and propylene glycol and the ethanol is from about 50% to about 60% w/w and the propylene glycol is from about 3% to about 7% w/w. Preferably, the formulation contains about 4% w/w naloxone, about 34.5% w/w water, about 55% w/w ethanol, about 0.05% L-menthol, and about 5% propylene glycol. In an embodiment, the formulation also contains about 0.005% or 0.02% w/w disodium edetate dihydrate.

In yet another embodiment, the formulations of the present invention are directed to sublingual spray formulations wherein the amount of naloxone is from about 8% to about 12% w/w, the amount of water is from about 25% to about 35% w/w, the amount of ethanol is from about 50% to about 60% w/w, the amount of propylene glycol is from about 3% to about 7% w/w, and the amount of antioxidant is from about 0.01% to about 0.03% w/w, wherein the % w/w is of the total formulation. Preferably, the formulation contains about 10.1% w/w naloxone, about 29.8% w/w water, about 55% w/w ethanol, and about 5% propylene glycol. In an embodiment, the formulation also contains about 0.005% or 0.02% w/w disodium edetate dihydrate.

In some embodiments, the formulations of the present invention contain citric acid as a pH adjustor.

Pharmaceutically acceptable salts that can be used in accordance with the current invention include but are not limited to hydrochloride dihydrate, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

In preferred embodiments the pharmaceutically acceptable salt is hydrochloride dihydrate.

Derivatives of naloxone that can be used in accordance with the current invention include but are not limited 3-O-acyl, phenylhydrazone, and methiodide derivatives.

The solvent used with the present invention is United States Pharmacopeia ("USP") purified water.

Cosolvents that can be used in accordance with the current invention are alcohols, and glycols or a mixture thereof.

Alcohols that can be used in accordance with the current invention include but are not limited to methanol, ethanol, propyl alcohol, and butyl alcohol.

Glycols that can be used in accordance with the current invention include but are not limited to propylene glycol, polypropylene glycol, and butylene glycol and polyethylene glycols such as PEG 200 and PEG 400 and the like.

In preferred embodiments, the cosolvent is ethanol or propylene glycol or a mixture thereof.

In another preferred embodiment, the amount of cosolvent included in the formulation is from about 5% to about 90% w/w. In other more preferred embodiments, the amount of cosolvent included in the formulation is about 5% w/w propylene glycol. In other more preferred embodiments, the amount of cosolvent included in the formulation is about 55% w/w ethanol.

In other more preferred embodiments the cosolvent is a mixture of propylene glycol at about 5% w/w and ethanol at about 55% w/w.

Solubilizers that can be used in accordance with the current invention are hydroxpropyl beta-cyclodextrin ("HPβCD") and sulfobutylether cyclodextrin or a mixture thereof.

In preferred embodiments the solubilizer is HPβCD.

In more preferred embodiments the amount of HPβCD is about 30% w/w.

Permeation enhancers that can be used in accordance with the current invention include but are not limited to menthol, Tween® 80 (Tween is a registered trademark of Uniqema Americas, LLC), sodium lauryl sulfate, glyceryl oleate, oleic acid, cetylpyridium chloride, and sodium desoxy cholate.

In preferred embodiments, the amount of permeation enhancer is from about 0.001% to about 0.1% w/w. In a more preferred embodiment, the formulations contain from about 0.01% to about 0.1% w/w permeation enhancer. In a most preferred embodiment, the formulations contain from about 0.02% to about 0.08% w/w permeation enhancer.

In preferred embodiment the permeation enhancer is menthol, the preferred amount of menthol is from about 0.001% to about 0.1% w/w. In a more preferred embodiment, the formulations contain from about 0.01% to about 0.1% w/w menthol. In an even more preferred embodiment, the formulations contain from about 0.02% to about 0.08% w/w menthol. In a most preferred embodiment, the formulations contain about 0.05% w/w menthol.

Formulations of the present invention may have a pH range from about 2 to about 7, preferably from about 4 to about 6 and more preferably from about 4.5 to about 5.5. pH adjustors that can be used in accordance with the present invention include but are not limited to citric acid. In preferred embodiments the amount of citric acid is from about 0.002% to about 0.015% w/w. In more preferred embodiments the amount of citric acid is about 0.002% w/w. In other more preferred embodiments the amount of citric acid is about 0.0025% w/w.

In yet another embodiment, the formulations of the present invention are capable of producing a droplet size distribution wherein the mean Dv(10) is from about 12 to about 25 microns during administration.

In a further embodiment, the formulations of the present invention are capable of producing a droplet size distribution wherein the mean Dv(50) is from about 25 to about 45 microns during administration.

In yet another embodiment, the formulations of the present invention are capable of producing a droplet size distribution wherein the mean Dv(90) is from about 300 to about 600 microns during administration. Preferably, the formulations of the present invention are capable of producing a droplet size distribution wherein the mean Dv(90) is from about 425 to about 500 microns during administration.

Formulations Without Alcohol

In a further embodiment, the invention is directed to storage stable sublingual spray formulations comprising an effective amount of naloxone, a pharmaceutically acceptable salt or a derivative thereof, water, and an antioxidant, and the formulations do not contain alcohol.

In a preferred embodiment, the sublingual spray formulation comprises from about 0.1% w/w to about 15% w/w naloxone or a salt or derivative thereof. In a more preferred embodiment, the sublingual spray formulation comprises from about 1% w/w to about 10% w/w naloxone or a salt or derivative thereof. In a most preferred embodiment, the formulations contain from about 3% w/w to about 6% w/w naloxone or a salt or derivative thereof.

In another embodiment, the formulations contain from about 20% w/w to about 99% water. In a preferred embodiment, the formulations contain from about 60% w/w to about 99% w/w water. In a more preferred embodiment, the formulations contain from about 80% w/w to about 99% w/w water. In a most preferred embodiment, the formulations contain from about 90% w/w to about 99% w/w water.

In an embodiment, the formulations contain from about 5% w/w to about 50% w/w glycerol. In a preferred embodiment, the formulations contain from about 10% w/w to about 40% w/w glycerol. In a more preferred embodiment, the formulations contain form about 15% w/w to about 35% w/w glycerol.

In another embodiment, the formulations contain from about 0.1% w/w to about 50% w/w polyethylene glycol 400. In a more preferred embodiment, the formulations contain from about 10% w/w to about 40% w/w polyethylene glycol 400.

In another embodiment, the formulation contains a pharmaceutically acceptable salt of naloxone. In a preferred embodiment, the formulation contains a salt selected from the group consisting of hydrochloride, citrate, halide, phosphate, sulfate, acetate, ascorbate, maleate, succinate, carbonate, mesylate and lactate. One of skill in the art could use other pharmaceutically acceptable naloxone salts in the formulations of the present invention.

In a preferred embodiment, the antioxidant is selected from the group consisting of ascorbic acid, cysteine HCl monohydrate, citric acid, ethylenediamine tetra acetic acid (EDTA), methionine, sodium citrate, sodium ascorbate, sodium thiosulfate, sodium metabisulfite, sodium bisulfite, glutathione and thioglycerol. Other appropriate antioxidants known by those of skill in the art could also be added to formulations of the present invention.

In a preferred embodiment, the formulations contain from about 0.0001% w/w to about 0.5% w/w of the antioxidant. In a more preferred embodiment, the formulations may contain from about 0.005% w/w to about 0.1% w/w of the antioxidant. In a most preferred embodiment, the formulations contain 0.05% of the antioxidant.

In another embodiment, the formulations of the present invention contain a chelating agent. In a preferred embodiment, the chelating agent is edetate disodium dihydrate.

In an embodiment, the formulations contain from about 0.001% to about 0.5% w/w of the chelating agent. In a preferred embodiment, the formulations contain from about 0.001% w/w to about 0.10% of the chelating agent. In a more preferred embodiment, the formulations contain about 0.05 of the chelating agent.

In a further embodiment, the formulation contains a permeation enhancer, a sweetener, a sweetness enhancer, a pH modifier, a flavoring agent, a preservative, or a combination thereof.

In another embodiment, the formulation contains a permeation enhancer. In a preferred embodiment, the permeation enhancer is selected from the group consisting of menthol, methyl chitosan, oleic acid, polysorbate 80, sodium edetate, cetylpyridinium chloride, sodium lauryl sulfate, citric acid, sodium desoxycholate, sodium deoxyglycolate, glyceryl oleate, glyceryl monosterate, Sodium hydroxybenzoyal amino caprylate, sodium caprate, dodecyl dimethyl aminopropionate and L-lysine.

In a preferred embodiment, the formulations contain a sweetener. In a more preferred embodiment, the sweetener is selected from the group consisting of sucralose, aspartame, saccharin, dextrose, mannitol, glycerin, and xylitol. In a preferred embodiment, the formulations contain from about 0.001% w/w to about 2% w/w of sweetener. In a more preferred embodiment, the formulations contain from about 0.05% w/w to about 1% w/w of the sweetener. In a most preferred embodiment, the formulations contain sucralose as sweetener at about 0.8% w/w.

In a further embodiment, the formulation may contain a sweetness enhancer, an ammonium salt form of crude and refined Glycyrrhizic Acid, for example, Magnasweet® product (available from Mafco Worldwide Corporation, Magnasweet is a registered trademark of Mafco Worldwide Corporation). Magnasweet® products use the ammonium salt forms of crude and refined Glycyrrhizic Acid. Glycyrrhizic Acid is also available as a pure derivative in the sodium and potassium salt forms.

In another embodiment, the formulations contain a pH modifier. In a preferred embodiment, the pH modifier adjusts the pH of the formulation to from about 2 to about 7. In a more preferred embodiment, the pH modifier adjusts the pH of the formulation to from about 2 to about 4. In most preferred embodiments, the pH modifier adjusts the pH of the formulations to about 2.5 or 3.

In another embodiment, the formulations contain a flavoring agent. In a preferred embodiment, the formulations contain a flavoring agent selected from the group consisting of peppermint oil, menthol, spearmint oil, citrus oil, cinnamon oil, strawberry flavor, cherry flavor, raspberry flavor, orange oil, and a combination thereof. Other appropriate flavoring agents known by those of skill in art could also be added to formulations of the present invention. In a preferred embodiment, the formulations contain from about 0.001% w/w to about 1% w/w of the flavoring agent. In a more preferred embodiment, the formulations contain from about 0.005% w/w to about 0.5% w/w of the flavoring agent. In a most preferred embodiment, the formulations contain strawberry as flavoring agent at about 0.08% w/w.

In yet another embodiment, the formulations may contain a preservative. In a preferred embodiment, the preservative is selected from the group consisting of butyl paraben, methyl paraben, ethyl paraben, propyl paraben, sodium benzoate, and benzoic acid. In a preferred embodiment, the formulations contain from about 0.001% w/w to about 1% w/w of the preservative. In a more preferred embodiment, the formulations contain from about 0.005% w/w to about 0.2% w/w of the preservative. In a most preferred embodiment, the formulations contain methyl paraben as a preservative at about 0.1% w/w.

In yet another embodiment, the formulations of the present invention are capable of producing a droplet size distribution wherein the mean Dv(10) is from about 12 to about 20 microns during administration.

In a further embodiment, the formulations of the present invention are capable of producing a droplet size distribution wherein the mean Dv(50) is from about 25 to about 35 microns during administration.

In yet another embodiment, the formulations of the present invention are capable of producing a droplet size distribution wherein the mean Dv(90) is from about 40 to about 150 microns during administration. Preferably, the formulations of the present invention are capable of producing a droplet size distribution wherein the mean Dv(90) is from about 60 to about 110 microns during administration.

All claims, aspects and embodiments of the invention, and specific examples thereof, are intended to encompass equivalents thereof.

In a further embodiment, the invention is directed to treating patients by administering the formulations (with or without alcohol) of the present invention to the patient. In preferred embodiment, the formulations are administered in order to treat opioid dependence, opioid overdose, and congenital insensitivity to pain with anhidrosis.

Definitions

As used herein, all numerical values relating to amounts, weights, and the like, that are defined as "about" each particular value is plus or minus 10%. For example, the phrase "about 10% w/w" is to be understood as "9% to 11% w/w." Therefore, amounts within 10% of the claimed value are encompassed by the scope of the claims.

As used herein "% w/w" refers to the percent weight of the total formulation.

As used herein the term "effective amount" refers to the amount necessary to treat a patient in need thereof.

As used herein the term "patient" refers but is not limited to a person that is being treated opioid dependence, opioid overdose, insensitivity to pain with anhidrosis, or another affliction or disease that can be treated with naloxone.

As used herein the phrase "pharmaceutically acceptable" refers to ingredients that are not biologically or otherwise undesirable in a sublingual dosage form.

As used herein, "storage stable" refers to formulations which maintain greater than 95% purity following at least four weeks of storage at about 40° C.

Preferably, the (alcohol and alcohol-free) formulations of the present invention are propellant free. As used herein, "propellant free" refers to a formulation that is not administered using compressed gas.

The following examples are intended to illustrate the present invention and to teach one of ordinary skill in the art how to make and use the invention. They are not intended to be limiting in any way.

EXAMPLES

Example 1

Preparation of Naloxone Formulations Containing Alcohol

Sublingual spray formulations were created by first degassing ethanol and USP purified water, separately. Next, the ethanol and purified water were each purged with nitrogen. Soluble excipients were then dissolved in either the ethanol or the purified water based on their solubility. Next, the solutions were combined. Naloxone was added to the final solution and mixed until dissolved.

Strawberry flavor was used as the source of the flavoring agent.

TABLE 1

Stable Sublingual Naloxone Spray Formulations

| Formulation | Control | #1A | #2A | #3A | #4A | #5A | #6A | #7A |
|---|---|---|---|---|---|---|---|---|
| Naloxone | 2.44 | 2.44 | 2.44 | 2.44 | 2.44 | 4.00 | 6.7 | 10.1 |
| Water (USP) | 37.56 | 37.55 | 37.55 | 37.54 | 37.54 | 34.45 | 33.23 | 29.83 |
| Alcohol | 55 | 55 | 55 | 55 | 55 | 55 | 55 | 55 |
| Propylene Glycol | 5 | 5 | 5 | 5 | 5 | 5 | 5 | 5 |
| L-menthol | | | | | | 0.05 | | |
| Sodium Thiosulfate | | 0.01 | 0.01 | | | | | |
| Citric Acid | | 0.0025 | | | | | | |
| Flavoring agent | | | | | | 0.08 | | |
| Edetate disodium dihydrate | | | 0.005 | 0.005 | 0.005 | 0.005 | 0.005 | 0.005 |
| BHA | | | | 0.01 | | | | |
| BHT | | | | 0.005 | | | | |
| Sodium Ascorbate | | | | | 0.02 | 0.02 | 0.02 | 0.02 | values = % w/w

Example 2

Stability Testing of Naloxone Formulations

The formulations listed in Table 1 were subjected to stability testing at 40° C. and 55° C.±2° C. under 75%±5% relative humidity for eight weeks. The stability data was collected at zero, one, two, three, four, and eight weeks at 55° C. and at zero, four, and eight weeks at 40° C. Assay and impurities were detected using high performance liquid chromatography with an ultraviolet detector. The assay was performed at 288 nm and indicated as a % of initial concentration. For all impurities, analysis was performed at 240 nm and expressed as a % area. Amounts of particular impurities are listed in Tables 2A to 2F and 3A to 3H as a percentage of the area of each formulation along with amount of total impurities. "BQL" refers to "Below Quantifiable Limit" and "ND" refers to "Not Detected."

Tables 2A to 2E. Stability Data for Sublingual Naloxone Spray Formulations Stored at 40° C.±2° C. Under 75%±5% Relative Humidity 2A. Stability of Control Stored at 40° C.

| Naloxone | RRT | T = 0 | 4 Weeks | 8 Weeks |
|---|---|---|---|---|
| Assay (%) | | | | |
| Impurity C | 0.66 | ND | 0.81% | 0.92% |
| Impurity A | 0.83 | ND | 0.37% | 0.51% |
| Impurity F | 0.93 | ND | ND | ND |
| Impurity D | 1.14 | ND | ND | ND |
| Impurity E | 2.85 | ND | 5.59% | 5.53% |
| Impurity B | 3.21 | ND | ND | ND |
| Unknown Impurities | 0.30 | ND | 0.13% | 0.18% |
| | 0.35 | ND | ND | ND |
| | 0.50 | ND | 0.28% | 0.46% |
| | 2.85 | ND | ND | ND |
| Total Impurities | | 0.00% | 7.18% | 7.60% |

2B. Stability of Form. #1A (with Sod. Thiosulphate & Citric Acid) Stored at 40° C.

| Naloxone | RRT | T = 0 | 4 Weeks | 8 Weeks |
|---|---|---|---|---|
| Assay (%) | | | | |
| Impurity C | 0.66 | ND | BQL | BQL |
| Impurity A | 0.83 | ND | BQL | BQL |
| Impurity F | 0.93 | ND | ND | ND |
| Impurity D | 1.14 | ND | ND | ND |
| Impurity E | 2.85 | ND | ND | ND |
| Impurity B | 3.21 | ND | ND | ND |
| Unknown Impurities | 0.32 | ND | ND | ND |
| | 0.52 | ND | ND | ND |
| | 2.67 | ND | ND | ND |
| | | ND | ND | ND |
| Total Impurities | | 0.00% | 0.00% | 0.00% |

2C. Stability of Form. #2A (with Sod. Thiosulphate & Edetate Disodium Dihydrate) Stored at 40° C.

| Naloxone | RRT | T = 0 | 4 Weeks | 8 Weeks |
|---|---|---|---|---|
| Assay (%) | | | | |
| Impurity C | 0.66 | ND | BQL | BQL |
| Impurity A | 0.83 | ND | BQL | BQL |
| Impurity F | 0.93 | ND | ND | ND |
| Impurity D | 1.14 | ND | ND | ND |
| Impurity E | 2.85 | ND | ND | ND |
| Impurity B | 3.21 | ND | ND | ND |
| | 0.50 | ND | ND | ND |
| Unknown Impurities | 0.52 | ND | ND | ND |
| | 0.74 | ND | ND | ND |
| | 1.37 | ND | ND | ND |

| 2C. Stability of Form. #2A (with Sod. Thiosulphate & Edetate Disodium Dihydrate) Stored at 40° C. | | | | |
|---|---|---|---|---|
| Naloxone | RRT | T = 0 | 4 Weeks | 8 Weeks |
| | 2.20 | ND | ND | ND |
| | 2.47 | ND | ND | ND |
| Total Impurities | | 0.00% | 0.00% | 0.00% |

| 2D. Stability of Form. #3A (with BHA & BHT) Stored at 40° C. | | | | |
|---|---|---|---|---|
| Naloxone | RRT | T = 0 | 4 Weeks | 8 Weeks |
| Assay (%) | | | | |
| Impurity C | 0.66 | ND | BQL | BQL |
| Impurity A | 0.83 | ND | BQL | BQL |
| Impurity F | 0.93 | ND | ND | ND |
| Impurity D | 1.14 | ND | ND | ND |
| Impurity E | 2.85 | ND | ND | ND |
| Impurity B | 3.21 | ND | ND | ND |
| Unknown Impurities | 0.31 | ND | ND | ND |
| | 0.50 | ND | ND | ND |
| | 1.79 | ND | ND | ND |
| | 1.83 | ND | ND | ND |
| | 2.10 | ND | ND | ND |
| | | ND | ND | ND |
| Total Impurities | | 0.00% | 0.00% | 0.00% |

| 2E. Stability of Form. #4A (with Sod. Ascorbate and Edetate Disodium Dihydrate) Stored at 40° C. | | | | |
|---|---|---|---|---|
| Naloxone | RRT | T = 0 | 4 Weeks | 8 Weeks |
| Assay (%) | | 100 | | |
| Impurity C | 0.66 | ND | BQL | BQL |
| Impurity A | 0.83 | ND | 0.15 | 0.19 |
| Impurity F | 0.93 | ND | ND | ND |
| Impurity D | 1.14 | ND | ND | ND |
| Impurity E | 2.85 | ND | ND | ND |
| Impurity B | 3.21 | ND | ND | ND |
| Unknown Impurities | 0.52 | ND | ND | BQL |
| | 1.79 | ND | ND | ND |
| | 1.83 | ND | ND | ND |
| | 2.10 | ND | ND | ND |
| Total Impurities | | 0.00% | 0.15% | 0.19% |

| 2F. Stability of Form. #5A (with Sod. Ascorbate and Edetate Disodium Dihydrate) Stored at 40° C. | | | | |
|---|---|---|---|---|
| Naloxone | RRT | T = 0 | 4 Weeks | 3 Months |
| Assay (%) | | 100 | 97.77 | 97.6 |
| Impurity C | 0.66 | ND | ND | 0.03 |
| Impurity A | 0.83 | 0.11 | 0.12 | 0.15 |
| Impurity F | 0.93 | ND | ND | ND |
| Impurity D | 1.14 | ND | ND | ND |
| Impurity E | 2.85 | ND | 0.13 | 0.13 |
| Impurity B | 3.21 | ND | ND | ND |
| Unknown Impurities | 0.52 | ND | ND | ND |
| | 0.79 | ND | ND | ND |
| | 1.83 | ND | ND | ND |
| | 2.10 | ND | ND | ND |
| | 2.32 | ND | ND | ND |
| | 3.23 | ND | ND | ND |
| | 3.94 | ND | ND | 0.04 |
| | 5.14 | ND | ND | ND |
| Total Impurities | | 0.00% | 0.25 | 0.29 |

Sublingual naloxone formulations of the present invention contained less than one percent total impurities after eight weeks at 40° C. This is a stark contrast to the control formulation which contained 7.6% impurities at the same time. Specifically, the formulations which contained sodium thiosulfate or BHA and BHT resulted in 0% detected impurities after eight weeks. Also, formulations which contain sodium ascorbate (0.02% wt/wt) and edetate disodium dihydrate (0.005% wt/wt) resulted in only 0.29% total impurities after 3 months.

Tables 3A to 3H. Stability Data for Sublingual Naloxone Spray Formulations Stored at 55° C.±2° C.

3A. Stability of Control Stored at 55° C.

| Naloxone | RRT | T = 0 | 1 Week | 2 Weeks | 3 Weeks | 4 Weeks | 8 Weeks |
|---|---|---|---|---|---|---|---|
| Assay (%) | | 100.00 | | | | | |
| Impurity C | 0.66 | ND | ND | ND | 0.54% | 0.33% | 0.35% |
| Impurity A | 0.83 | ND | ND | ND | 1.31% | 1.39% | 1.59% |
| Impurity F | 0.93 | ND | ND | ND | ND | ND | ND |
| Impurity D | 1.14 | ND | ND | ND | ND | ND | ND |
| Impurity E | 2.85 | ND | ND | ND | ND | ND | ND |
| Impurity B | 3.21 | ND | ND | ND | ND | ND | ND |
| Unknown Impurities | 0.30 | ND | ND | ND | ND | 0.1 | 0.32% |
| | 0.35 | ND | ND | ND | 0.15% | 0.16% | 0.08% |
| | 0.50 | ND | ND | ND | 0.83% | 0.81% | 0.67% |
| | 2.85 | ND | ND | ND | 4% | 7.50% | 6.65% |
| Total Impurities | | 0.00% | 0.00% | 0.00% | 6.83% | 10.29% | 9.66% |

3B. Stability of Form. #1A (with Sod. Thiosulphate & Citric Acid) Stored at 55° C.

| Naloxone | RRT | T = 0 | 1 Week | 2 Weeks | 3 Weeks | 4 Weeks | 8 Weeks |
|---|---|---|---|---|---|---|---|
| Assay (%) | | 100.00 | | | | | |
| Impurity C | 0.66 | ND | ND | ND | 0.12% | 0.37% | 0.29% |
| Impurity A | 0.83 | ND | ND | ND | 0.14% | 0.67% | 1.01% |
| Impurity F | 0.93 | ND | ND | ND | ND | ND | ND |
| Impurity D | 1.14 | ND | ND | ND | ND | ND | ND |
| Impurity E | 2.85 | ND | ND | ND | 0.55% | 1.88% | 1.52% |
| Impurity B | 3.21 | ND | ND | ND | ND | ND | ND |
| Unknown Impurities | 0.32 | ND | ND | ND | ND | 0.09% | 0.25% |
| | 0.52 | ND | ND | ND | 0.06% | 0.51% | 0.59% |
| | 2.67 | ND | ND | ND | ND | ND | ND |
| | | ND | ND | ND | ND | ND | ND |
| Total Impurities | | 0.00% | 0.00% | 0.00% | 0.87% | 3.52% | 3.66% |

3C. Stability of Form. #2A (with Sod. Thiosulphate & Edetate Disodium Dihydrate) Stored at 55° C.

| Naloxone | RRT | T = 0 | 1 Week | 2 Weeks | 3 Weeks | 4 Weeks | 8 Weeks |
|---|---|---|---|---|---|---|---|
| Assay (%) | | 100.00 | | | | | |
| Impurity C | 0.66 | ND | ND | ND | ND | BQL | BQL |
| Impurity A | 0.83 | ND | ND | ND | BQL | 0.07% | 0.11% |
| Impurity F | 0.93 | ND | ND | ND | ND | ND | ND |
| Impurity D | 1.14 | ND | ND | ND | ND | ND | ND |
| Impurity E | 2.85 | ND | ND | ND | ND | ND | ND |
| Impurity B | 3.21 | ND | ND | ND | ND | ND | ND |
| | 0.31 | ND | ND | ND | ND | ND | ND |
| Unknown Impurities | 0.52 | ND | ND | ND | ND | ND | 0.08% |
| | 0.74 | ND | ND | ND | ND | ND | ND |
| | 1.37 | ND | ND | ND | ND | ND | ND |
| | 2.20 | ND | ND | ND | ND | ND | ND |
| | 2.47 | ND | ND | ND | ND | ND | ND |
| Total Impurities | | 0.00% | 0.00% | 0.00% | 0.00% | 0.07% | 0.19% |

3D. Stability of Form. #3A (with BHA & BHT) Stored at 55° C.

| Naloxone | RRT | T = 0 | 1 Week | 2 Weeks | 3 Weeks | 4 Weeks | 8 Weeks |
|---|---|---|---|---|---|---|---|
| Assay (%) | | 100.00 | | | | | |
| Impurity C | 0.66 | ND | ND | ND | ND | ND | BQL |
| Impurity A | 0.83 | ND | ND | ND | BQL | 0.07% | 0.13% |
| Impurity F | 0.93 | ND | ND | ND | ND | ND | ND |

3D. Stability of Form. #3A (with BHA & BHT) Stored at 55° C.

| Naloxone | RRT | T = 0 | 1 Week | 2 Weeks | 3 Weeks | 4 Weeks | 8 Weeks |
|---|---|---|---|---|---|---|---|
| Impurity D | 1.14 | ND | ND | ND | ND | ND | ND |
| Impurity E | 2.85 | ND | ND | ND | ND | ND | ND |
| Impurity B | 3.21 | ND | ND | ND | ND | ND | ND |
| Unknown Impurities | 0.31 | ND | ND | ND | ND | ND | ND |
|  | 0.50 | ND | ND | ND | ND | ND | 0.08% |
|  | 1.79 | ND | ND | ND | ND | ND | ND |
|  | 1.83 | ND | ND | ND | ND | ND | ND |
|  | 2.10 | ND | ND | ND | ND | ND | ND |
|  |  | ND | ND | ND | ND | ND | ND |
| Total impurities |  | 0.00% | 0.00% | 0.00% | 0.00% | 0.07% | 0.21% |

3E. Stability of Form. #4A (with Sod. Ascorbate and Edetate Disodium Dihydrate) Stored at 55° C.

| Naloxone | RRT | T = 0 | 1 Week | 2 Weeks | 3 Weeks | 4 Weeks | 8 Weeks |
|---|---|---|---|---|---|---|---|
| Assay (%) |  | 100.00 |  |  |  |  |  |
| Impurity C | 0.66 | ND | ND | ND | ND | ND | 0.06% |
| Impurity A | 0.83 | ND | ND | ND | 0.11% | 0.19% | 0.19% |
| Impurity F | 0.93 | ND | ND | ND | ND | ND | ND |
| Impurity D | 1.14 | ND | ND | ND | ND | ND | ND |
| Impurity E | 2.85 | ND | ND | ND | ND | ND | ND |
| Impurity B | 3.21 | ND | ND | ND | ND | ND | ND |
| Unknown Impurities | 0.52 | ND | ND | ND | ND | ND | BQL |
|  | 1.79 | ND | ND | ND | ND | ND | ND |
|  | 1.83 | ND | ND | ND | ND | ND | ND |
|  | 2.10 | ND | ND | ND | ND | ND | ND |
| Total Impurities |  | 0.00% | 0.00% | 0.00% | 0.11% | 0.19% | 0.25% |

3F. Stability of Form. # 5A (with Sod. Ascorbate and Edetate Disodium Dihydrate) Stored at 55° C.

| Naloxone | RRT | T = 0 | 2 Weeks | 4 Weeks | 6 Weeks | 8 Weeks |
|---|---|---|---|---|---|---|
| Assay (%) |  | 100 | 102.37 | 98.75 | 98.51 | 100.76 |
| Impurity C | 0.66 | ND | ND | ND | ND | 0.05% |
| Impurity A | 0.83 | 0.11 | 0.14 | 0.15 | 0.19 | 0.17% |
| Impurity F | 0.93 | ND | ND | ND | ND | ND |
| Impurity D | 1.14 | ND | ND | ND | ND | ND |
| Impurity E | 2.85 | ND | 0.13 | 0.11 | 0.12 | 0.12% |
| Impurity B | 3.21 | ND | ND | ND | ND | ND |
| Unknown Impurities | 0.49 | ND | ND | ND | 0.06 | 0.05% |
|  | 0.79 | ND | ND | ND | 0.03 | BQL |
|  | 1.83 | ND | ND | ND | ND | ND |
|  | 2.10 | ND | ND | ND | ND | ND |
|  | 2.32 | ND | ND | ND | ND | ND |
|  | 3.05 | ND | ND | ND | ND | ND |
|  | 3.90 | ND | BQL | 0.05 | 0.07 | 0.05% |
|  | 5.14 | ND | ND | ND | ND | ND |
| Total Impurities |  | 0.00% | 0.27 | 0.31 | 0.47 | 0.44% |

3H. Stability of Form. #6A (with Sod. Ascorbate and Edetate Disodium Dihydrate) Stored at 55° C.

| Naloxone | RRT | T = 0 | 2 Weeks | 4 Weeks | 8 Weeks |
|---|---|---|---|---|---|
| Assay (%) |  | 100.00 | 101.35 | 102.69 | 102.99 |
| Impurity C | 0.66 | ND | BQL | BQL | 0.08% |
| Impurity A | 0.81 | BQL | 0.08% | 0.19% | 0.18% |
| Impurity F | 0.93 | ND | ND | ND | ND |
| Impurity D | 1.14 | ND | ND | ND | ND |
| Impurity E | 2.85 | 0.04% | 0.07% | 0.06% | 0.10% |
| Impurity B | 3.21 | ND | ND | ND | 0.12% |
| Unknown Impurities | 0.33 | ND | ND | ND | ND |
|  | 0.50 | ND | ND | ND | 0.06% |
|  | 0.57 | ND | ND | ND | ND |

-continued

3H. Stability of Form. #6A (with Sod. Ascorbate and Edetate Disodium Dihydrate) Stored at 55° C.

| Naloxone | RRT | T = 0 | 2 Weeks | 4 Weeks | 8 Weeks |
|---|---|---|---|---|---|
| | 0.61 | ND | ND | ND | ND |
| | 3.43 | ND | ND | ND | ND |
| Total Impurities | | 0.04% | 0.15% | 0.25% | 0.54% |

3G. Stability of Form. #7A (with Sod. Ascorbate and Edetate Disodium Dihydrate) Stored at 55° C.

| | RRT | T = 0 | 2 Weeks | 4 Weeks | 8 Weeks |
|---|---|---|---|---|---|
| Assay (%) | | 100.00 | 100.91 | 100.92 | 102.05 |
| Impurity C | 0.66 | ND | 0.06% | 0.05% | 0.11% |
| Impurity A | 0.81 | BQL | 0.11% | 0.22% | 0.17% |
| Impurity F | 0.93 | ND | ND | ND | ND |
| Impurity D | 1.14 | ND | ND | ND | ND |
| Impurity E | 2.85 | 0.06% | 0.07% | 0.06% | 0.11% |
| Impurity B | 3.21 | ND | ND | ND | 0.13% |
| Unknown | 0.33 | ND | ND | ND | ND |
| Impurities | 0.50 | ND | ND | ND | 0.05% |
| | 0.57 | ND | ND | ND | ND |
| | 0.61 | ND | ND | ND | ND |
| | 2.41 | 0.00 | 0.00 | 0.00 | 0.05% |
| | 3.43 | ND | ND | ND | ND |
| Total Impurities | | 0.06% | 0.24% | 0.33% | 0.62% |

Similar to the stability study at 40° C., all of the formulations of the present invention had significantly fewer impurities at eight weeks compared to the control. The superior stability characteristics of the formulations of the present invention will allow the formulations to be effective when used by patients.

Example 3

Droplet Testing

In order to determine the spray profile of Formulation #5A, it was subjected to standardized droplet testing. A challenge of creating a Naloxone sublingual spray formulation is that it must be capable of producing spray droplets that are over 10 microns in diameter. Spray droplets 10 microns or smaller could be inhaled into the lungs. The optimal particle size for sublingual spray droplets is from 20 to about 200 microns in diameter. It is desirable for the formulation to have droplet sizes near 20 because this increases the surface area and increased surface area exposure is one factor that contributes to a high bioavailability. Sublingual formulations should be able to maintain a consistent droplet size throughout its shelf life.

Droplet analysis was conducted using standard laser analysis procedures known by those of skill in the art. Droplet size distribution (Dv10, Dv50, Dv90, and Span were tested at two distances, 3 cm and 6 cm). Dv10 refers to droplet size for which 10% of the total volume is obtained; Dv50 refers to droplet size for which 50% of the total volume is obtained; Dv90 refers to droplet size for which 90% of the total volume is obtained; Span refers to distribution span (Dv90−Dv10)/Dv50; % RSD refers to the percent relative standard deviation. The results of these tests can be seen below in Tables 4 to 9. Applicant found during testing that formulations of the present invention yielded desirable droplet sizes for sublingual administration. The testing also revealed that the formulation dose remains consistent when administered with a spray pump.

TABLE 4

Spray Profile of Naloxone Spray Formulation #5A, Particle Size at 3 cm

| | | Particle Size | | | | |
|---|---|---|---|---|---|---|
| | Formulation #5A | DV(10) | DV(50) | DV(90) | % < 10 μ | Span |
| 3 cm | Actuation 1 | 14.79 | 28.92 | 389.9 | 1.225 | 12.97 |
| | Actuation 2 | 17.98 | 32.05 | 455.6 | 0.001 | 13.65 |
| | Actuation 3 | 13.46 | 36.92 | 584.8 | 4.747 | 15.48 |
| | Average | 15.41 | 32.63 | 476.8 | 1.991 | 14.03 |

TABLE 5

Spray Profile of Naloxone Spray Formulation #5A, Particle Size at 6 cm

| | | Particle Size | | | | |
|---|---|---|---|---|---|---|
| | Formulation #5A | DV(10) | DV(50) | DV(90) | % < 10 μ | Span |
| 6 cm | Actuation 1 | 20.58 | 38.64 | 498.6 | 1.918 | 12.37 |
| | Actuation 2 | 18.67 | 37.59 | 529.4 | 1.537 | 13.59 |
| | Actuation 3 | 21.26 | 36.44 | 452.3 | 1.767 | 11.83 |
| | Average | 20.17 | 37.56 | 493.4 | 1.741 | 12.60 |

TABLE 6

Spray Profile of Naloxone Spray Formulation #5A, Spray Pattern at 3 cm

| | | Spray Pattern | | |
|---|---|---|---|---|
| | Formulation #5A | Dmin (mm) | Dmax (mm) | Ovality Ratio |
| 3 cm | Actuation 1 | 21.2 | 33.4 | 1.577 |
| | Actuation 2 | 23.5 | 31.5 | 1.342 |
| | Actuation 3 | 17.6 | 30.9 | 1.755 |
| | Average | 20.8 | 31.9 | 1.558 |

TABLE 7

Spray Profile of Naloxone Spray Formulation #5A, Spray Pattern at 6 cm

| | | Spray Pattern | | |
|---|---|---|---|---|
| | Formulation #5A | Dmin (mm) | Dmax (mm) | Ovality Ratio |
| 6 cm | Actuation 1 | 24.5 | 55.6 | 2.268 |
| | Actuation 2 | 34.3 | 49.7 | 1.447 |
| | Actuation 3 | 33.9 | 52 | 1.535 |
| | Average | 30.9 | 52.4 | 1.750 |

TABLE 8

Spray Profile of Naloxone Spray Formulation #5A, Plume geometry data at 3 cm

| | | Plume Geometry | |
|---|---|---|---|
| | Formulation #5A | Width (mm) | Angle (°) |
| 3 cm | Actuation 1 | 28.7 | 51.1 |
| | Actuation 2 | 25.5 | 45.9 |
| | Actuation 3 | 35.4 | 60.4 |
| | Average | 29.9 | 52.5 |

TABLE 9

Spray Profile of Naloxone Spray Formulation #5A,
Plume geometry data at 6 cm

| | Formulation #5A | Plume Geometry | |
| --- | --- | --- | --- |
| | | Width (mm) | Angle (°) |
| 6 cm | Actuation 1 | 54.3 | 48.4 |
| | Actuation 2 | 52.6 | 47.3 |
| | Actuation 3 | — | — |
| | Average | 53.5 | 47.9 |

As can be seen in Tables 4 to 9, Formulation #5A of the present invention provided excellent plume geometry and spray patterns.

Example 4

Preparation of Naloxone Formulations that are Alcohol-Free

In order to prepare a naloxone sublingual formulation, the components as indicated in "Table 10. The Components of Formulation #1AF" below were weighed. The components were mixed until a clear solution was formed.

Naloxone HCL dihydrate base U.S.P. was used as the source of naloxone in the formulations that follow. Methyl paraben, U.S.P., (available from Spectrum) was used as the preservative source. Strawberry flavor, Nat&Art 915.0543 U, (available from FONA) was used as the source of flavoring agent. Edetate Disodium Dihydrate, U.S.P., (available from Spectrum) was used as the source of chelating agent or as antioxidant. Water, U.S.P., purified, (available from RICCA) was used as the source of solvent.

TABLE 10

The Components of Formulation #1AF

| Ingredients | % w/w |
| --- | --- |
| Naloxone HCl Dihydrate | 4.82 |
| Sucralose | 0.80 |
| Methyl Paraben | 0.10 |
| Flavoring agent | 0.08 |
| Edetate Disodium Dihydrate | 0.05 |
| Water USP | 94.15 |
| | 100.0 |

Example 5

Preparation of Additional Naloxone Sublingual Formulations

In order to prepare naloxone sublingual formulations, the components as indicated in "Table 11. The Components of Control and Formulations #1AF to #6AF" below were weighed. The components were mixed until a clear solution was formed. Strawberry flavoring was used as the source of flavoring agent.

TABLE 11

The Components of Control and Formulations #1AF to #6AF

| Formulation | Control | #1AF | #2AF | #3AF | #4AF | #5AF | #6AF |
| --- | --- | --- | --- | --- | --- | --- | --- |
| Naloxone HCL Dihydrate | 4.83 | 4.82 | 4.89 | 4.89 | 4.89 | 4.83 | 4.82 |
| Water (USP) | 94.19 | 94.15 | 95.01 | 94.08 | 93.98 | 94.16 | 94.15 |
| Sucralose | 0.8 | 0.8 | | 0.8 | 0.8 | 0.8 | 0.8 |
| Methyl Paraben | 0.1 | 0.1 | | 0.1 | 0.1 | 0.1 | 0.1 |
| Flavoring | 0.08 | 0.08 | 0.08 | 0.08 | 0.08 | 0.08 | 0.08 |
| Edetate Disodium Dihydrate | | 0.05 | 0.005 | 0.05 | 0.05 | 0.005 | 0.05 |
| L-cysteine Hydrochloride Monohydrate | | | | | 0.1 | | |
| Sodium Ascorbate | | | 0.02 | | | 0.02 | |
| pH | 3.03 | 2.5 | 4.46 | 4.16 | 2.56 | 3.02 | 3 |

Example 6

Stability Testing of Naloxone Formulations

The formulations listed in Table 11 were subjected to stability testing at 40° C. and 55° C.±2° C. under 75%±5% relative humidity for eight weeks. The stability data was collected at zero, one, two, three, four, at 55° C. and at zero, four weeks at 40° C. Assay and impurities were detected using high performance liquid chromatography with an ultraviolet detector. The assay was performed at 288 nm and indicated as a % of initial concentration. For all impurities, analysis was performed at 240 nm and expressed as a % area. Amounts of particular impurities are listed in Tables 12A to 12G and 13A to 13C as a percentage of the area of each formulation along with amount of total impurities. "BQL" refers to "Below Quantifiable Limit" and "ND" refers to "Not Detected." "Ppm" refers to parts per million.

Tables 12A to 12G. Stability Data for Sublingual Naloxone Spray Formulations Stored at 55° C.

12A

| Stability of Control Stored at 55° C. | | | |
| --- | --- | --- | --- |
| Naloxone | RRT | T = 0 | 1 Week 55° C. |
| Assay (%) | | 100 | 101.48 |
| Impurity C | 0.66 | ND | ND |
| Impurity A | 0.83 | 0.15 | 0.15 |
| Impurity F | 0.93 | ND | ND |
| Impurity D | 1.14 | ND | ND |
| Impurity E | 3.20 | 0.07 | 0.62 |
| Impurity B | 3.40 | ND | ND |
| Unknown Impurities | 0.27 | ND | ND |
| | 0.33 | ND | BQL |
| | 0.36 | ND | ND |
| | 0.40 | ND | ND |
| | 0.49 | ND | 0.07 |
| | 0.56 | ND | ND |
| | 0.59 | ND | 0.12 |
| | 3.52 | ND | ND |
| Total Impurities | | 0.22% | 0.96% |

| 12B. Stability of Form. #2AF (with Sod. acorbate & Edetate Disodium Dihydrate) Stored at 55° C. | | | | | | |
|---|---|---|---|---|---|---|
| Naloxone | RRT | T = 0 | 1 Week | 2 Weeks | 3 Weeks | 4 Weeks |
| pH | | 4.469 | 4.21 | 4.239 | 4.02 | 4.224 |
| Assay (%) | | 100 | 99.6 | 101.48 | 98.07 | 98.00 |
| Impurity C | 0.66 | ND | BQL | BQL | BQL | BQL |
| Impurity A | 0.83 | BQL | 0.09 | 0.28 | 0.27 | 0.18% |
| Impurity F | 0.93 | ND | ND | ND | ND | ND |
| Impurity D | 1.14 | ND | ND | ND | ND | ND |
| Impurity E | 3.20 | ND | ND | ND | ND | ND |
| Impurity B | 3.40 | ND | ND | ND | ND | ND |
| Unknown | 0.33 | ND | BQL | 0.07 | 0.1 | 0.13 |
| Impurities | 0.36 | ND | BQL | ND | ND | ND |
| | 0.40 | ND | ND | ND | ND | ND |
| | 0.49 | ND | ND | 0.05 | 0.07 | 0.07% |
| | 0.56 | ND | 0.08 | 0.08 | 0.09 | 0.08 |
| | 0.59 | ND | 0.07 | 0.12 | 0.14 | 0.14 |
| | 3.90 | ND | 0.09 | 0.15 | 0.13 | 0.14 |
| Total Impurities | | 0.00% | 0.33 | 0.82 | 0.80 | 0.74% |

| 12C. Stability of Form. #3AF (Edetate Disodium Dihydrate) Stored at 55° C. | | | | | | |
|---|---|---|---|---|---|---|
| Naloxone | RRT | T = 0 | 1 Weeks | 2 Weeks | 3 Weeks | 4 Weeks |
| pH | | 4.16 | 4.23 | 4.168 | 3.94 | 4.33 |
| Assay (%) | | 100 | 100.5 | 100.7 | 98.03 | 98.63 |
| Impurity C | 0.66 | ND | ND | ND | ND | ND |
| Impurity A | 0.83 | BQL | BQL | 0.21 | 0.18 | 0.07 |
| Impurity F | 0.93 | ND | ND | ND | ND | ND |
| Impurity D | 1.14 | ND | ND | ND | ND | ND |
| Impurity E | 3.20 | 0.13 | 0.11 | 0.09 | 0.09 | 0.08 |
| Impurity B | 3.40 | ND | ND | ND | ND | ND |
| Unknown | 0.33 | ND | BQL | 0.11 | 0.12 | 0.18 |
| Impurities | 0.36 | ND | BQL | BQL | BQL | BQL |
| | 0.40 | ND | ND | ND | ND | ND |
| | 0.49 | ND | ND | 0.09 | 0.1 | 0.11% |
| | 0.56 | ND | ND | ND | ND | ND |
| | 0.59 | ND | 0.12 | 0.11 | 0.14 | 0.15 |
| | 3.67 | ND | ND | ND | ND | 0.07 |
| | 3.90 | ND | 0.08 | 0.14 | 0.13 | 0.13 |
| Total Impurities | | 0.13% | 0.31% | 0.72% | 0.76% | 0.79% |

| 12D. Stability of Form. #4AF (Edetate Disodium Dihydrate and L-Cysteine hydrochloride) Stored at 55° C. | | | | | | |
|---|---|---|---|---|---|---|
| Naloxone | RRT | T = 0 | 1 Week | 2 Weeks | 3 Weeks | 4 Weeks |
| pH | | 2.56 | 2.5 | 2.44 | 2.38 | 2.413 |
| Assay (%) | | 100 | 98.5 | 100.03 | 97.87 | 98.59 |
| Impurity C | 0.66 | ND | ND | 0.13 | 0.11 | 0.09% |
| Impurity A | 0.83 | BQL | ND | 0.22 | 0.29 | 0.17% |
| Impurity F | 0.93 | ND | ND | ND | ND | ND |
| Impurity D | 1.14 | ND | ND | ND | ND | ND |
| Impurity E | 3.20 | ND | ND | ND | ND | ND |
| Impurity B | 3.40 | ND | ND | ND | ND | ND |
| Unknown | 0.33 | ND | ND | ND | ND | ND |
| Impurities | 0.36 | ND | ND | ND | ND | ND |
| | 0.40 | ND | ND | ND | ND | ND |
| | 0.49 | ND | ND | ND | ND | ND |
| | 0.56 | ND | ND | 0.05 | 0.07 | 0.06 |
| | 0.59 | ND | ND | ND | ND | ND |
| | 3.52 | ND | ND | ND | ND | ND |
| Total Impurities | | 0.00% | 0.00% | 0.40% | 0.47% | 0.32% |

12E. Stability of Form. #5AF (Edetate Disodium dihydrate and Sodium ascorbate) Stored at 55° C.

| Naloxone | RRT | T = 0 | 1 Week | 2 Weeks |
|---|---|---|---|---|
| pH | | NP | NP | 3.185 |
| Assay (%) | | 100 | 98.37 | 98.12 |
| Impurity C | 0.66 | ND | BQL | BQL |
| Impurity A | 0.83 | 0.15 | 0.18 | 0.11 |
| Impurity F | 0.93 | ND | ND | ND |
| Impurity D | 1.14 | ND | ND | ND |
| Impurity E | 3.20 | 0.07 | 0.16 | 0.12 |
| Impurity B | 3.40 | ND | ND | ND |
| Unknown Impurities | 0.27 | ND | ND | ND |
| | 0.33 | ND | ND | ND |
| | 0.36 | ND | ND | ND |
| | 0.40 | ND | ND | ND |
| | 0.49 | ND | BQL | BQL |
| | 0.56 | ND | ND | BQL |
| | 0.59 | ND | ND | ND |
| | 3.52 | ND | ND | ND |
| Total Impurities | | 0.22% | 0.34% | 0.23% |

12F. Stability of Form. #6AF (Edetate Disodium Dihydrate) Stored at 55° C.

| Naloxone | RRT | T = 0 | 1 Week | 2 Weeks | 3 Weeks | 4 Weeks |
|---|---|---|---|---|---|---|
| pH | | 3.013 | 3.443 | 3.132 | 3.241 | 3.21 |
| Assay (%) | | 100.00% | 98.34% | 98.36% | 98.34% | 100.07% |
| Impurity C | 0.66 | 0.10% | 0.10% | 0.21% | 0.13% | 0.13% |
| Impurity A | 0.83 | BQL | BQL | BQL | BQL | BQL |
| Impurity F | 0.93 | ND | ND | ND | ND | ND |
| Impurity D | 1.14 | ND | 0.83 ppm | 1.79 ppm | 1.74 ppm | ND |
| Impurity E | 3.20 | 0.15% | 0.15% | 0.15% | 0.17% | 0.17% |
| Impurity B | 3.40 | ND | ND | ND | ND | ND |
| Unknown Impurities | 0.27 | ND | ND | ND | ND | ND |
| | 0.33 | ND | ND | ND | ND | ND |
| | 0.36 | ND | ND | ND | ND | ND |
| | 0.40 | ND | ND | ND | ND | ND |
| | 0.49 | ND | BQL | 0.06% | 0.06% | 0.12% |
| | 0.56 | ND | ND | ND | ND | ND |
| | 0.59 | ND | ND | ND | ND | ND |
| | 0.77 | ND | ND | BQL | BQL | 0.05% |
| | 3.90 | ND | ND | ND | ND | ND |
| | 4.62 | ND | ND | BQL | BQL | ND |
| Total Impurities | | 0.25% | 0.25% | 0.42% | 0.36% | 0.47% |

12G. Stability of Form. #1AF (Edetate Disodium Dihydrate) Stored at 55° C.

| Naloxone | RRT | T = 0 | 1 Week | 2 Weeks | 3 Weeks | 4 Weeks |
|---|---|---|---|---|---|---|
| pH | | 2.505 | 2.907 | 2.581 | 2.616 | 2.62 |
| Assay (%) | | 100.00% | 107.80% | 100.51% | 100.17% | 102.39% |
| Impurity C | 0.66 | 0.10% | 0.10% | 0.10% | 0.10% | 0.09% |
| Impurity A | 0.83 | BQL | BQL | BQL | BQL | BQL |
| Impurity F | 0.93 | ND | ND | ND | ND | ND |
| Impurity D | 1.14 | NP | 0.95 ppm | 1.25 ppm | 1.59 ppm | ND |
| Impurity E | 3.20 | 0.15% | 0.14% | 0.15% | 0.16% | 0.18% |
| Impurity B | 3.40 | ND | ND | ND | ND | ND |
| Unknown Impurities | 0.06 | 0.13% | 0.13% | 0.13% | 0.13% | ND |
| | 0.27 | ND | ND | ND | ND | ND |
| | 0.33 | ND | ND | ND | ND | ND |
| | 0.36 | ND | ND | ND | ND | ND |
| | 0.40 | ND | ND | ND | ND | ND |
| | 0.47 | ND | ND | ND | ND | ND |
| | 0.49 | ND | BQL | 0.08% | 0.06% | 0.05% |
| | 0.56 | ND | ND | ND | ND | ND |
| | 0.77 | ND | ND | ND | BQL | BQL |
| | 3.61 | ND | ND | ND | BQL | ND |
| | 3.90 | ND | ND | ND | ND | ND |
| | 4.63 | ND | ND | ND | BQL | ND |
| Total Impurities | | 0.38% | 0.37% | 0.46% | 0.45% | 0.32% |

Sublingual naloxone formulations of the present invention contained less than 0.8% of total impurities after four weeks at 55° C. This is a stark contrast to the control formulation which contained 0.96% impurities after 1 week at 55° C. Specifically, the formulations which contained sodium ascorbate or edetate disodium dihydrate exhibited lower impurities after four weeks. Additionally, the formulations with a pH of about 2 to about 3 which contained edetate disodium dehydrate were very stable.

Tables 13A to 13C. Stability Data for Sublingual Naloxone Spray Formulations Stored at 40° C. Under 75% Relative Humidity

13A

Stability of Form.#2AF (with Sod. acorbate & Edetate Disodium Dihydrate) Stored at 40° C. under 75% Relative Humidity

| Naloxone | RRT | T = 0 | 4 Weeks |
|---|---|---|---|
| pH | | 4.469 | 4.394 |
| Assay (%) | | 100 | 98.12 |
| Impurity C | 0.66 | ND | 0.06 |
| Impurity A | 0.83 | BQL | 0.12 |
| Impurity F | 0.93 | ND | ND |
| Impurity D | 1.14 | ND | ND |
| Impurity E | 3.20 | ND | ND |
| Impurity B | 3.40 | ND | ND |
| Unknown | 0.33 | ND | BQL |
| Impurities | 0.36 | ND | ND |
| | 0.40 | ND | ND |
| | 0.49 | ND | 0.06 |
| | 0.56 | ND | ND |
| | 0.59 | ND | 0.06 |
| | 3.90 | ND | 0.14 |
| Total Impurities | | 0.00% | 0.44% |

13B

Stability of Form. #3AF (Edetate Disodium Dihydrate) Stored at 40° C. under 75% Relative Humidity

| Naloxone | RRT | T = 0 | 4 Weeks |
|---|---|---|---|
| pH | | 4.16 | 4.596 |
| Assay (%) | | 100 | 99.69 |
| Impurity C | 0.66 | ND | ND |
| Impurity A | 0.83 | BQL | BQL |
| Impurity F | 0.93 | ND | ND |
| Impurity D | 1.14 | ND | ND |
| Impurity E | 3.20 | 0.13 | ND |
| Impurity B | 3.40 | ND | ND |

13B-continued

Stability of Form. #3AF (Edetate Disodium Dihydrate) Stored at 40° C. under 75% Relative Humidity

| Naloxone | RRT | T = 0 | 4 Weeks |
|---|---|---|---|
| Unknown | 0.33 | ND | BQL |
| Impurities | 0.36 | ND | ND |
| | 0.40 | ND | ND |
| | 0.49 | ND | BQL |
| | 0.56 | ND | ND |
| | 0.59 | ND | 0.11 |
| | 3.67 | ND | ND |
| | 3.90 | ND | 0.11 |
| Total Impurities | | 0.13% | 0.22% |

13C

Stability of Form. #4AF (Edetate Disodium Dihydrate and L-Cysteine hydrochloride) Stored at 40° C. under 75% Relative Humidity

| Naloxone | RRT | T = 0 | 4 Weeks |
|---|---|---|---|
| pH | | 2.56 | 2.502 |
| Assay (%) | | 100 | 97.08 |
| Impurity C | 0.66 | ND | ND |
| Impurity A | 0.83 | BQL | BQL |
| Impurity F | 0.93 | ND | ND |
| Impurity D | 1.14 | ND | ND |
| Impurity E | 3.20 | ND | ND |
| Impurity B | 3.40 | ND | ND |
| Unknown | 0.33 | ND | ND |
| Impurities | 0.36 | ND | ND |
| | 0.40 | ND | ND |
| | 0.49 | ND | ND |
| | 0.56 | ND | ND |
| | 0.59 | ND | ND |
| | 3.52 | ND | ND |
| Total Impurities | | 0.00% | 0.00% |

The naloxone formulations of the present invention contained less than 0.45% of total impurities after four weeks at 40° C.

Example 7

Freeze/Thaw Testing

In order to further determine the stability of Formulations #1AF and #6AF, the formulations were subjected to standard freeze/thaw stability testing. The results are below in "Table 14. Stability of Formulations #1AF and #6AF to Freeze/Thaw Testing."

TABLE 14

Stability of Formulations #1AF and #6AF to Freeze/Thaw Testing

| | Formulation #1AF to #6AF | | | | | | |
|---|---|---|---|---|---|---|---|
| Drug Substance | t = 0 | Cycle 1, −20° C. | Cycle 1, 25° C. | Cycle 2, −20° C. | Cycle 2, 25° C. | Cycle 3, −20° C. | Cycle 3, 25° C. |
| Date Observed: | Mar. 12, 2015 | Mar. 16, 2015 | Mar. 18, 2015 | Mar. 20, 2015 | Mar. 22, 2015 | Mar. 24, 2015 | Mar. 26, 2015 |
| Physical appearance clear | clear | clear | clear | clear | clear | clear | clear |
| Color colorless | colorless | colorless | colorless | colorless | colorless | colorless | colorless |

The naloxone formulations of the present invention were clear and colorless after several cycles of freezing and thawing. This study further demonstrates the stability of the formulations.

Example 8

Droplet Testing

In order to determine the spray profile of Formulation #1AF, it was subjected to standardized droplet testing. As previously explained, the optimal particle size for sublingual spray droplets is from 20 to about 200 microns in diameter. It is desirable for the formulation to have droplet sizes near 20 because this increases the surface area and increased surface area exposure is one factor that contributes to a high bioavailability. Sublingual formulations should be able to maintain a consistent droplet size throughout its shelf life.

Droplet analysis was conducted using standard laser analysis procedures known by those of skill in the art. Droplet size distribution (Dv10, Dv50, Dv90, and Span were tested at two distances, 3 cm and 6 cm). Dv10 refers to droplet size for which 10% of the total volume is obtained; Dv50 refers to droplet size for which 50% of the total volume is obtained; Dv90 refers to droplet size for which 90% of the total volume is obtained; Span refers to distribution span (Dv90−Dv10)/Dv50; % RSD refers to the percent relative standard deviation. The results of these tests can be seen below in Tables 15 to 20. Applicant found during testing that formulations of the present invention yielded desirable droplet sizes for sublingual administration. The testing also revealed that the formulation dose remains consistent when administered with a spray pump

TABLE 15

Spray Profile of naloxone Spray Formulation #1AF, Particle Size at 3 cm

| Formulation #1AF | | Particle Size | | | | |
|---|---|---|---|---|---|---|
| | | DV(10) | DV(50) | DV(90) | % < 10 μ | Span |
| 3 cm | Actuation 1 | 13.16 | 26.23 | 63.21 | 2.792 | 1.908 |
| | Actuation 2 | 11.52 | 27 | 90.85 | 6.547 | 2.939 |
| | Actuation 3 | 12.95 | 28.39 | 144 | 3.505 | 4.615 |
| | Average | 12.54 | 27.21 | 99.4 | 4.281 | 3.15 |

TABLE 16

Spray Profile of Naloxone Spray Formulation #1AF, Particle Size at 6 cm

| Formulation #1AF | | Particle Size | | | | |
|---|---|---|---|---|---|---|
| | | DV(10) | DV(50) | DV(90) | % < 10 μ | Span |
| 6 cm | Actuation 1 | 20.18 | 32.51 | 53.9 | 1.198 | 1.037 |
| | Actuation 2 | 18.02 | 31.45 | 58.48 | 0.024 | 1.286 |
| | Actuation 3 | 16.81 | 33.44 | 77.92 | 1.799 | 1.828 |
| | Average | 18.34 | 32.47 | 63.4 | 1.007 | 1.38 |

TABLE 17

Spray Profile of Naloxone Spray Formulation #1AF, Spray Pattern at 3 cm

| Formulation #1AF | | Spray Pattern | | |
|---|---|---|---|---|
| | | Dmin (mm) | Dmax (mm) | Ovality Ratio |
| 3 cm | Actuation 1 | 26.5 | 41.3 | 1.557 |
| | Actuation 2 | 24.8 | 43.5 | 1.751 |
| | Actuation 3 | 29 | 40.6 | 1.402 |
| | Average | 26.8 | 41.8 | 1.570 |

TABLE 18

Spray Profile of Naloxone Spray Formulation #1AF, Spray Pattern at 6 cm

| Formulation #1AF | | Spray Pattern | | |
|---|---|---|---|---|
| | | Dmin (mm) | Dmax (mm) | Ovality Ratio |
| 6 cm | Actuation 1 | 52.6 | 68.6 | 1.304 |
| | Actuation 2 | 40.3 | 61.4 | 1.524 |
| | Actuation 3 | 47.5 | 59.7 | 1.256 |
| | Average | 46.8 | 63.2 | 1.361 |

TABLE 19

Spray Profile of Naloxone Spray Formulation #1AF, Plume geometry data at 3 cm

| Formulation #1AF | | Plume Geometry | |
|---|---|---|---|
| | | Width (mm) | Angle (°) |
| 3 cm | Actuation 1 | 39.7 | 66.7 |
| | Actuation 2 | 37.7 | 64.3 |
| | Actuation 3 | 33.5 | 58 |
| | Average | 37.0 | 63.0 |

TABLE 20

Spray Profile of Naloxone Spray Formulation #1AF, Plume geometry data at 6 cm

| Formulation #1AF | | Plume Geometry | |
|---|---|---|---|
| | | Width (mm) | Angle (°) |
| 6 cm | Actuation 1 | 63 | 54.9 |
| | Actuation 2 | 67.1 | 58.3 |
| | Actuation 3 | 68 | 59 |
| | Average | 66.0 | 57.4 |

As can be seen in Tables 15 to 20, Formulation #1AF of the present invention provided excellent plume geometry and spray patterns.

The invention claimed is:

1. A storage stable sublingual spray formulation comprising:
   from about 1% to about 10% w/w naloxone, or a pharmaceutically acceptable salt thereof;
   from about 30% to about 40% w/w water;
   from about 50% to about 60% w/w ethanol;
   from about 3% to about 7% w/w propylene glycol;
   from about 0.005% to about 0.08% w/w of an antioxidant; and
   from about 0.002% to 0.008% of a chelating agent,
   wherein the % w/w is of the total formulation.
2. The sublingual spray formulation of claim 1, wherein the chelating agent is edetate disodium dihydrate.

3. The sublingual spray formulation of claim 2, wherein the antioxidant is selected from the group consisting of butylated hydroxyanisole, butylated hydroxytoluene, sodium ascorbate, sodium thiosulfate, and a combination thereof.

4. A method of treating opioid dependence comprising administering the sublingual spray formulation of claim 1 to a patient in need thereof.

5. A method of treating opioid overdose comprising administering the sublingual spray formulation of claim 1 to a patient in need thereof.

6. A method of treating congenital insensitivity to pain with anhidrosis comprising administering the sublingual spray formulation of claim 1 to a patient in need thereof.

* * * * *